(12) United States Patent
DiRe

(10) Patent No.: US 7,448,680 B2
(45) Date of Patent: *Nov. 11, 2008

(54) CHAIR-SIDE MULTIMEDIA COMMUNICATION SYSTEM

(76) Inventor: Mark L. DiRe, 12917 SE. 38th St., Suite 202, Bellevue, WA (US) 98006

( * ) Notice: Subject to any disclaimer, the term of this patent is extended or adjusted under 35 U.S.C. 154(b) by 0 days.

This patent is subject to a terminal disclaimer.

(21) Appl. No.: 12/026,232

(22) Filed: Feb. 5, 2008

(65) Prior Publication Data

US 2008/0143156 A1 Jun. 19, 2008

Related U.S. Application Data

(63) Continuation of application No. 10/616,185, filed on Jul. 8, 2003, now Pat. No. 7,347,492.

(60) Provisional application No. 60/395,193, filed on Jul. 10, 2002.

(51) Int. Cl.
- A61G 15/00 (2006.01)
- A61G 15/10 (2006.01)
- A61G 15/14 (2006.01)
- A47C 7/72 (2006.01)

(52) U.S. Cl. .............. 297/217.3; 297/217.4; 297/217.6; 297/330

(58) Field of Classification Search .............. 297/217.3, 297/217.4, 217.6, 330
See application file for complete search history.

(56) References Cited

U.S. PATENT DOCUMENTS

| | | | |
|---|---|---|---|
| 3,311,411 A | 3/1967 | Page et al. | |
| 3,415,571 A | 12/1968 | Heimert, III | |
| 3,514,153 A | 5/1970 | Maurer et al. | |
| 3,591,234 A | 7/1971 | Condon | |
| 3,950,086 A | 4/1976 | Schulman et al. | |
| 4,109,958 A | 8/1978 | Grupelli | |
| 4,260,376 A | 4/1981 | Litel et al. | |
| 4,310,307 A | 1/1982 | Bellisario | |
| 4,727,416 A | 2/1988 | Cooper et al. | |
| 4,854,301 A | 8/1989 | Nakajima | |

(Continued)

FOREIGN PATENT DOCUMENTS

CH 683394 A5 3/1994

(Continued)

OTHER PUBLICATIONS

Technology and Lighting Center, Information online webpage, Seltzer Institute, Inc. URL+www.dentalchairpotato.com, downloaded Apr. 25, 2006.

Primary Examiner—Rodney B. White
(74) Attorney, Agent, or Firm—Seed IP Law Group PLLC

(57) ABSTRACT

A chair-side patient communication system for use with a chair having at least one armrest, the system including a display screen and light mounted in association with the chair, a computer system coupled to the display screen; a controller mounted in the armrest of the chair for controlling the computer system to provide access to the information to be displayed on the display screen; and at least one speaker mounted in the headrest of the chair. The system enables a user in the chair to remain stationary while controlling the display of the information via the controller on the armrest of the chair.

19 Claims, 4 Drawing Sheets

U.S. PATENT DOCUMENTS

| | | |
|---|---|---|
| 4,880,270 A | 11/1989 | Cooper |
| 4,915,450 A | 4/1990 | Cooper |
| 5,056,864 A | 10/1991 | Cooper |
| 5,765,910 A | 6/1998 | Larkin et al. |
| 5,779,305 A | 7/1998 | Hocking |
| 5,803,547 A | 9/1998 | Brown |
| 5,803,905 A | 9/1998 | Allred et al. |
| 5,854,624 A | 12/1998 | Grant |
| 5,884,350 A | 3/1999 | Kurze |
| 6,092,868 A | 7/2000 | Wynn |
| 6,093,019 A | 7/2000 | Morandi et al. |
| 6,102,476 A | 8/2000 | May et al. |
| 6,145,926 A | 11/2000 | Lin |
| 6,184,804 B1 | 2/2001 | Harrison |
| 6,270,157 B1 | 8/2001 | Kapushinski |
| 6,428,124 B1 | 8/2002 | Bluth et al. |
| 6,592,185 B2 | 7/2003 | Lew |
| 6,916,065 B2 | 7/2005 | Park |
| 7,347,492 B2 * | 3/2008 | DiRe ........................ 297/217.3 |
| 2002/0070590 A1 | 6/2002 | Carstens |
| 2004/0195876 A1 | 10/2004 | Huiban |

FOREIGN PATENT DOCUMENTS

| | | |
|---|---|---|
| EP | 251643 A2 | 1/1988 |
| EP | 584439 A1 | 3/1994 |
| KR | 200247914 | 7/2000 |

* cited by examiner

CHAIR-SIDE MULTIMEDIA COMMUNICATION SYSTEM

BACKGROUND OF THE INVENTION

1. Field of the Invention

The present invention pertains to a system for providing information to customers of service providers, and more particularly to a dental chair display and control system that provides multiple forms of communication, including Internet access, real time video imaging, and digital photography.

2. Description of the Related Art

Numerous types of services are provided in which a consumer must remain stationary for a substantial period of time. Examples of such services include dentistry, hair styling, manicuring, and the like. A common aspect of these services is that the consumer or patient is generally awake and alert while the service is being provided.

While an individual is receiving a service under these conditions, they are frequently unable to engage in activities to distract themselves. For example, listening to entertainment via headphones will interfere with the hair stylist's ability to cut and style hair. In addition, experience has shown that removable headphones are uncomfortable, confining, heavy, hot, tend to disturb the hair, and must be offered and accepted. Reading presents additional difficulties because it typically interferes with the service provider's ability to render effective and safe care, such as in the case of dentistry. A dentist must have unobstructed access to the patient's mouth, which would clearly be impaired by a patient attempting to bring a book or other reading material in front of their face in order to read.

Devices have been proposed for providing distraction and entertainment to dental patients in particular. U.S. Pat. No. 4,260,376 discloses a dental apparatus that provides an illumination source in combination with an audio-visual display to reduce or mask the effects of pain stimulus on a dental patient. The apparatus includes a television for displaying images generated from a video recording camera or prerecorded images from a cassette. While this apparatus might have been suitable for its purpose at the time it was developed in 1981, it does not have the capability of providing Internet access, digital photography, or access to patient records.

BRIEF SUMMARY OF THE INVENTION

The disclosed embodiments of the invention are directed to a patient communication system that includes, in one embodiment, a display screen with operatory light, an arm rest controller for a patient, and directional speakers in a headrest that provide sound in limited directions. Ideally the display screen is a flat panel touch screen.

In accordance with another embodiment of the invention, a miniature color video camera is included with the display screen and operatory light for providing real time imaging of the patient's mouth. Ideally, a second set of controls is provided that are remote from the armrest of the chair to enable the service provider to control the display screen and peripheral connections.

In accordance with yet another aspect of the present invention, the system includes access to the service provider's web page via the Internet, and in a preferred embodiment is limited to the service provider's website. Ideally, the system includes software to enable patient navigation of the website and dental staff access and management of the system, as well as a residential server that is preferably adjacent to the chair. Alternatively, a CPU can be mounted in the display screen case that is suspended over the patient in or on the chair or the display screen support.

In accordance with a further aspect of the present invention, a chair-side multimedia communication system is provided that includes the chair, an arm rest controller for an occupant of the chair; a display screen having at least an operatory light and coupled to the controller; and directional speakers coupled to the controller and mounted in a headrest on the chair to provide sound in a limited direction. A miniature color video camera is also mounted in conjunction with the display screen and suspended over the chair via a mounting arm. A digital camera can also be included for still pictures.

BRIEF DESCRIPTION OF THE SEVERAL VIEWS OF THE DRAWINGS

The foregoing features and advantages of the present invention will be more readily appreciated as the same become better understood from the following detailed description when taken in conjunction with the accompanying drawings wherein.

DETAILED DESCRIPTION OF THE INVENTION

Figure 1:
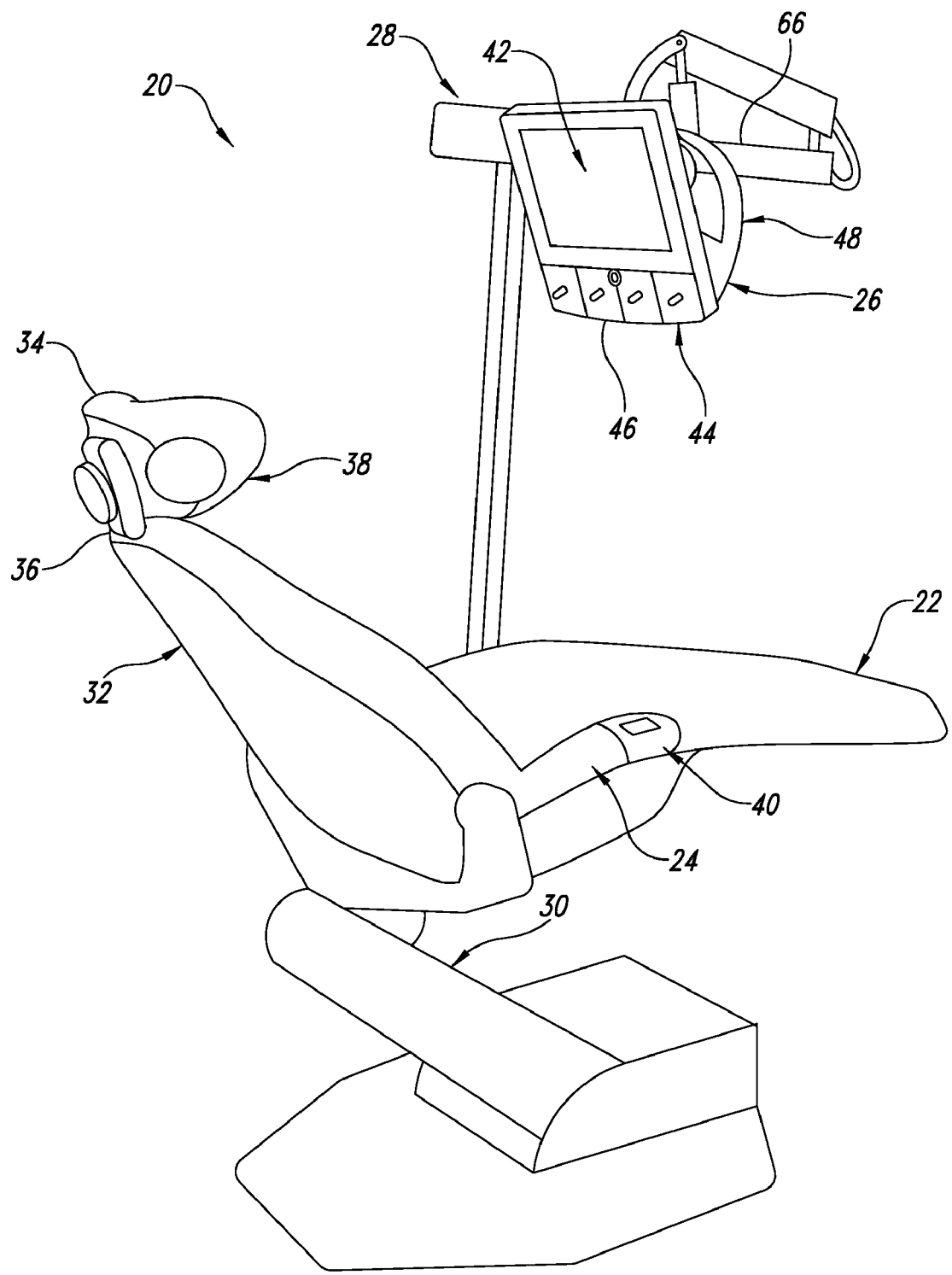
FIG. 1 is an isometric projection of a chair-side multimedia communication system formed in accordance with the present invention.

Referring initially to FIG. 1, shown therein is a chair-side multimedia communication system 20 formed in accordance with the present invention to include a chair 22 having at least one arm 24 associated therewith and a display screen and operatory light housing 26 suspended above the chair 22 by a stand 28. As shown in FIG. 1, the system 20 in this embodiment is used in conjunction with a dental chair 22. It is to be understood, however, that the system 20 may be adapted for use in other applications, such as a barber or hair stylist chair, and is not to be limited to a dental chair. However, certain features and components may not be needed, desirable, or usable, and hence modification of the system will be required.

The chair 22 is supported on a conventional adjustable support 30 that is readily commercially available and will not be described in detail herein. The chair 22 includes a backrest 32 having a headrest 34 attached at the top 36 thereof. Incorporated into the headrest 34 are directional speakers 38. The speakers 38 are well known and commercially available, and as such they will not be described in more detail herein. As shown in FIG. 1, the speakers 38 are mounted on each side of the headrest 34 and can be adjustable to give the patient personal control of the ambient operatory noise level and sound direction. The directional speaker design reduces patient directed sound levels from adding to the sound levels of the operatory area, thereby avoiding disturbing the dental staff or adjacent rooms. The use of integrated speakers instead of headsets or earphones reduces the number of choices to be made and makes usage universal.

Control of the volume of the speakers 38 is done by the user via a control pad 40 mounted on or in the arm 24. The control pad 40 can include the use of a touch pad, a roller ball, a mouse, or other known form of user input that can be manipulated with the hand. Preferably, the controller 40 is designed as a touch pad that is integrated into the arm 24. This location provides a conveniently fixed site and facilitates cleaning of the control pad 40 and reduces the risk of damage. Thus, the control pad 40 will be clean, simple, manageable, and trouble free.

The control pad 40 is also used to determine the output of a display screen 42 mounted in the housing 26. Intraoral operatory lights 44 are mounted on or in association with the housing 26 below the display screen 42. In the embodiment shown in FIG. 1, there are four lights 44 positioned horizontally across the bottom of the housing 26. The preferred position where a reclining patient can view the display screen 42 clearly is at the source of the intraoral light source, which in this case is the operatory lights 44. The viewing angle at the location from which the housing 26 is suspended from the stand 28 is unobstructed by other operatory equipment and dental personnel. It is to be understood that the lights 44 may be designed to be mounted or positioned independent of the housing 26, although they are preferably contained within the housing 26 as shown in FIG. 1.

Figure 2:
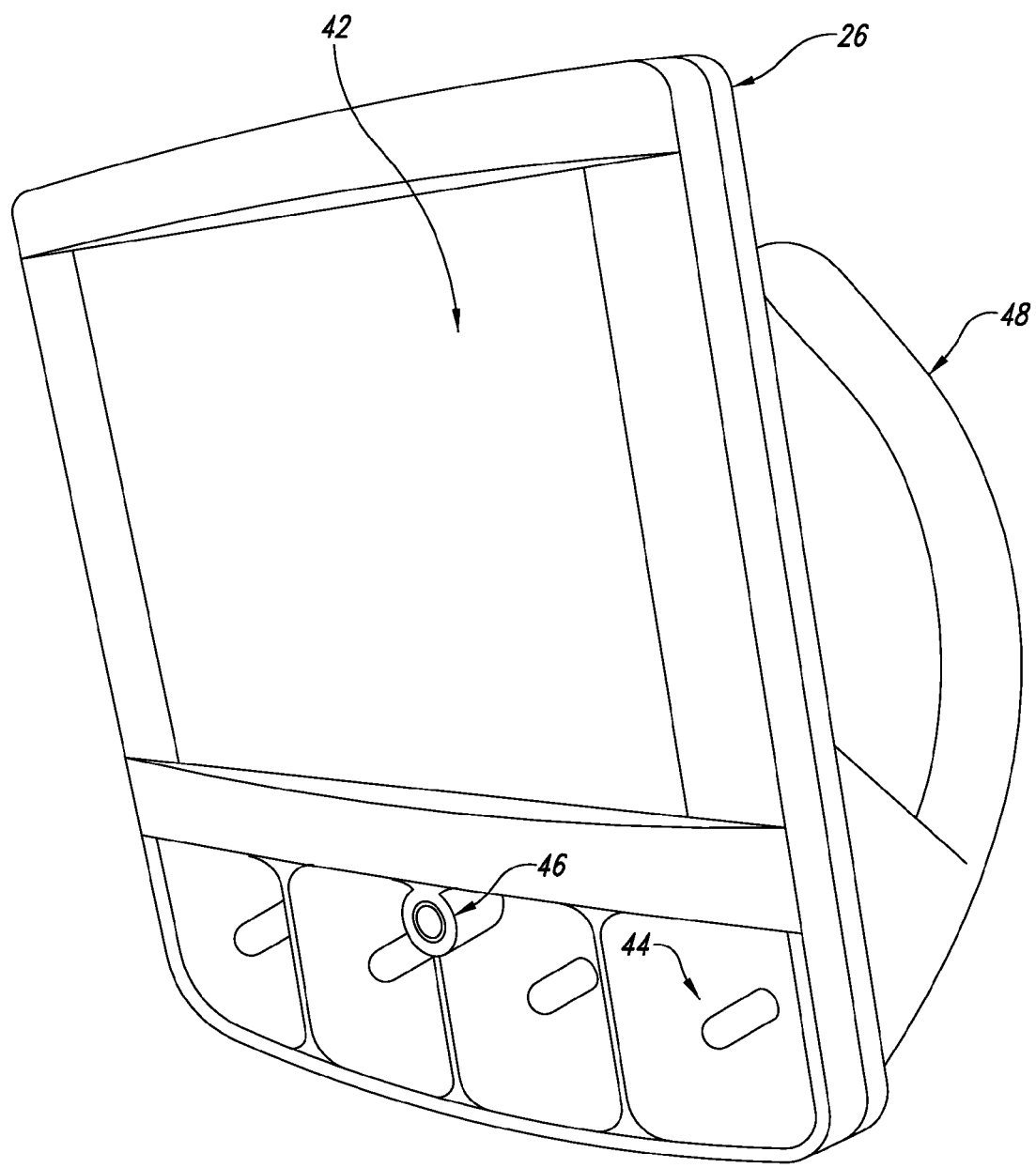
FIG. 2 is an enlarged view of a display screen housing formed in accordance with the system of FIG. 1.

Also mounted in the housing 26 is a miniature color video camera 46 (shown more clearly in FIG. 2) that is positioned and configured to display a patient's face, perioral area, and an intraoral image on the display screen 42. This form of "video mirror" provides visual feedback to the patient during treatment discussion by dental personnel. Presently, this type of feedback is provided with a handheld mirror, which has the disadvantage of blocking the light source, is difficult to position for viewing, and is inconvenient. Furthermore, there are patients who prefer to watch the treatment procedure as it is being completed, and the camera 46 will provide an unobstructed view for those patients desiring to use it.

Demonstration and patient education during dental hygiene appointments can be clearly viewed by the patient and effectively presented by the hygienist and the auxiliary dental team. Thus, this "video mirror" can be utilized and appreciated by the entire dental staff and patients alike. Handles 48 mounted to the back of the housing 26 are curved outward to provide a continuous surface for grasping and adjusting the position of the housing 26.

Figure 3:
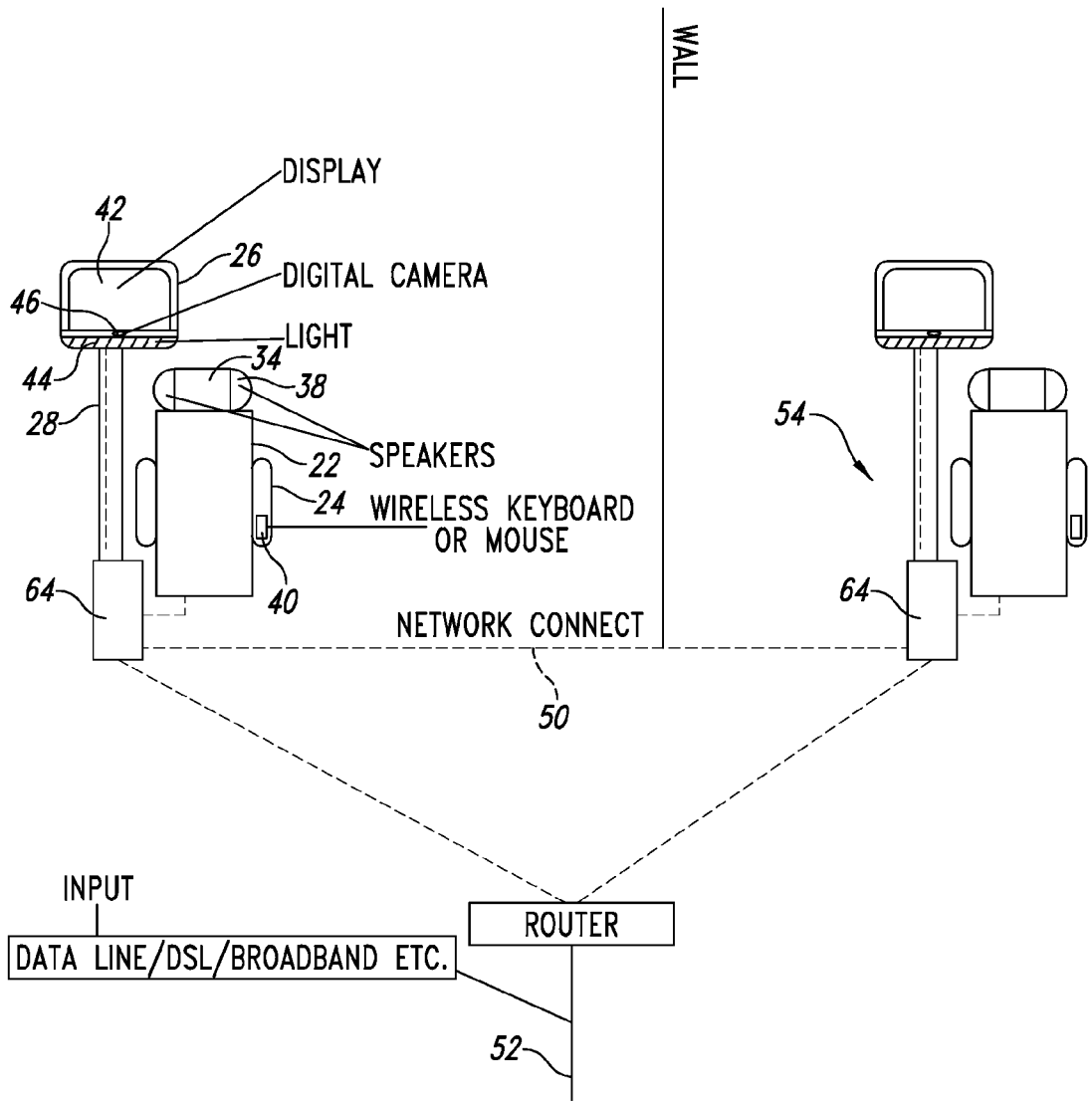
FIG. 3 is a block diagram of one embodiment of a multi-chair multimedia communication system formed in accordance with the present invention.

The display screen 42 is electrically coupled via an intraoffice network 50 to a high-speed broadband or DSL Internet line 52, as shown in FIG. 3. Also shown therein is a second chair-side system 54 that is connected to the network 50 and the high-speed broadband or DSL Internet line 52. Thus, the system can be expanded to include additional chairs as desired and as will be readily appreciated by one of ordinary skill.

The connection to the Internet will be fully operable. However, in one embodiment access can be limited to selected websites, such as the service provider's website to supply an organized entertainment venue for the patient that can include music, video, sports, magazines, movies, games, and the like.

Figure 4:
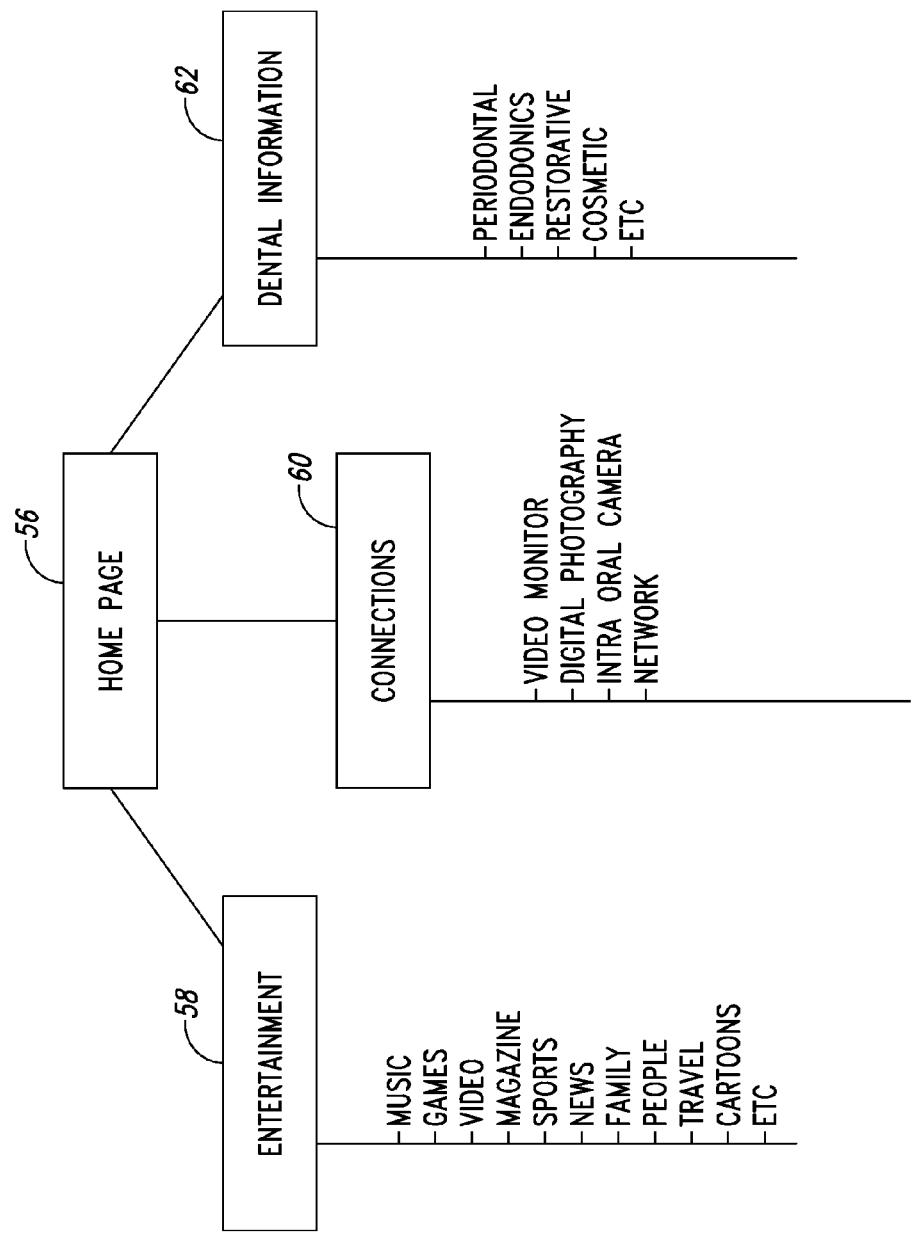
FIG. 4 is a tree diagram illustrating menu choices provided by software formed in accordance with one embodiment of the invention.

FIG. 4 shows a tree-like menu of selections available to a user starting at a home page 56 and choosing, for example, connections 60, video camera 46, and the third selection of dental information 62. Beneath each of these choices are additional selections. For example, under connections 60 is the option to chose digital photography. A digital camera (not shown) can be connected via USB cabling to the CPU 64 to provide viewing for still facial or intraoral photographs.

The patient can control the displayed content by using the control pad 40. These devices are rendered functional by the software resident in a server 64 that is ideally mounted on, in, or in close proximity to the chair 22, as shown in FIG. 3. The software is configured to accommodate use by not only the patient but also the dental staff. With respect to the patient, the software must be configured to provide easy access to the entertainment, and thus is designed so that all choices are on the desktop display on the screen 42 and accessible with either point-and-click type of control or a touch sensitive screen. Ideally, access by the patient is by the control pad 40 in order to limit the amount of movement required by the patient to control the system 20.

The desktop view will include the entertainment choices, dental information controls, and can also include several advertiser sites located on a permanent index border. Advertisers can be charged to display their product information on the provider's system 20.

Use of the system by the dental staff is also important and must be available via the point-and-click access or on the touch screen for those areas that the dental team will find most useful. For example, a treatment information catalogue can be provided with photographs, video clips, and written information about various dental conditions and treatments. This information can be displayed for viewing while treatment progresses or used as a visual aid in a treatment discussion. Dental hygienists, dental treatment assistants, and dentists will all find this information and its easy access extremely useful. This can also be an important tool in giving a patient a better understanding and informed consent about conditions diagnosed, planned treatment, and treatment that is neglected or declined. This information can be routed to a printer for creating a permanent record and providing a written copy to the patient.

The software should also provide easy access to the camera 46 in order to display home care procedures or conditions that are easily seen without magnification. As discussed above, the camera 46 can also be controlled by the patient to monitor the progress of a procedure if desired.

The software should also be configured to enable networking to a dental office software package or network computer for storing digital photographs and other dental records. In many offices, this can take the form of intraoral digital photographs and/or digital x-rays. In addition, the use of an intraoral video camera device to display a patient's current oral condition is becoming very popular. These devices magnify the image of the teeth to help visualize about one to three teeth at a time. It has proven to be an effective tool in patient education and treatment planning. The system of the present invention is configured to enable "plug and play" use of most intraoral video cameras.

As also discussed above, another diagnostic tool in dentistry is the use of still digital photography. Such cameras offer extremely high quality images from full face to single tooth magnification. The diagnostic quality and integration of image altering software is a significant feature and useful tool in dental diagnosis, treatment planning, and patient education. A USB connection into the system 20 allows for immediate display of still digital photographic images. The network connection 50 can be used for peripheral network storage, management, and display in another room at another time.

The system 20 of the present invention can be retrofitted to existing dental patient chairs and intraoral lights. One approach is to provide the system components in a kit form. A technician will need to disconnect the existing intraoral light at a vertical-horizontal knuckle and remove the intraoral light. The housing 26 is connected to a new horizontal arm member 66. Necessary wire connectors are fed through the port stand 28 to the floor at the sight of the chair 22. The technician can connect the CPU screen and operatory light housing 26, the speakers 38, and the control pad 40. The speakers are integrated into a new replacement headrest and the wiring is run under the chair 22 or the chair padding to the CPU. The control pad 40 can be configured to attach to the arm 24 on the chair 22 or the entire arm 24 can be replaced by removing the existing arm and running the wiring under the chair padding to connect to the CPU. The CPU will then be connected to the network 50 and to the DSL or broadband connection via a router 68. Conventional wiring can be used to make the necessary connections or wireless technology may also be used as known to those skilled in the art.

As will be readily appreciated from the foregoing, the system 20 of the present invention provides the ability to deliver web-based contents. Overall web access can be limited in order to centralize and control the content to be more dental office user specific or specific to the type of the service being provided. Entertainment and informational content is accessible via easy-to-use point and click formats. The dental team will also be able to access prepared dental-specific educational areas, and the video mirror for demonstrations. This configuration makes the system 20 an effective educational and sales tool for the dental team and a ubiquitous entertainment and informational experience for the dental patient.

While a preferred embodiment of the information has been illustrated and described, it is to be understood that various changes may be made therein without departing from the spirit and scope of the invention. For example, the configuration of the housing can be altered as necessary to meet the needs of a particular application. Consequently, the invention is not to be limited except by the scope of the claims that follow and the equivalents thereof.

The invention claimed is:

1. A patient communication system, comprising:
   a display screen for displaying an X-ray image visible to a patient in a dental chair;
   at least one operatory light mounted in relation to the dental chair such that the light provides intraoral light suitable for performing a dental procedure while the image is visible to the patient in the chair;
   a controller in communication with the display screen, the controller configured to select the image displayed by the display screen; and
   software configured to provide access to a network such that the display screen selectively displays an image from the network.

2. The patient communication system of claim 1, further comprising speakers located in a headrest associated with the dental chair.

3. The patient communication system of claim 2, wherein the speakers are capable of effectively directing sound to the patient in the dental chair while not significantly increasing ambient sound levels in an operatory area surrounding the dental chair.

4. The patient communication system of claim 3, further comprising a digital camera mounted in association with the display screen and coupled thereto for providing imaging of the patient in the dental chair.

5. The patient communication system of claim 1, wherein the display screen comprises a flat panel touch screen having the intraoral operatory light suspended over a patient chair such that the display screen and operatory light are visible from the chair to provide unobstructed viewing of the display screen by the patient and to provide light into the patient's mouth without interfering with access to the patient's mouth by the dental staff; and
   wherein the controller is associated with an armrest of the chair and configured to enable input commands by the patient through the controller to a computer associated with the display screen to provide patient access to a computer network.

6. The patient communication system of claim 5, further comprising directional speakers located in a headrest associated with the patient chair, the directional speakers configured to provide sound in limited directions, and wherein the computer is configured to provide access to a webpage of the service provider via the Internet.

7. A patient communication system, comprising:
   a patient chair;
   a display screen and intraoral operatory light suspended over the patient chair to provide unobstructed viewing of the display screen by the patient and to illuminate the patient's mouth without interfering with access to the patient's mouth by dental staff;
   a controller configured to enable patient input through use of the patient's hand and fingers;
   a computer system coupled to the display screen and the controller for providing access to the Internet; and
   a digital camera mounted in association with the display screen and coupled thereto for providing imaging of the patient in the dental chair.

8. The patient communication system of claim 7, further comprising speakers located in a headrest associated with the chair, the speakers configured to provide sound directly to the patient when the patient is in the chair.

9. The patient communication system of claim 7 wherein the computer is configured to provide access to a webpage of the service provider.

10. The patient communication system of claim 7, further comprising at least one additional controller remote from the chair to enable a service provider to control the computer and digital camera.

11. The patient communication system of claim 7, wherein the digital camera comprises a digital video camera to provide real time imaging.

12. A patient communication system, comprising:
    a display screen comprising a flat panel touch screen having an intraoral operatory light suspended over a patient chair such that the display screen and operatory light are visible from the chair to provide unobstructed viewing of the display screen by the patient and to provide light into the patient's mouth without interfering with access to the patient's mouth by the dental staff; and
    a controller associated with an armrest of the chair and configured to enable input commands by a patient through the controller to a computer associated with the display screen to provide patient access to a computer network.

13. The patient communication system of claim 12, further comprising directional speakers located in a headrest associated with the patient chair, the directional speakers configured to provide sound in limited directions; wherein the computer is configured to provide access to a webpage of the service provider via the Internet.

14. The patient communication system of claim 12 wherein the computer comprises a server coupled to the display screen and coupled to the controller in the armrest.

15. The patient communication system of claim 12 further comprising a video camera mounted in association with the display screen for providing real time imaging, wherein the video camera comprises a digital video camera.

16. A patient communication system, comprising:
a display screen comprising a flat panel touch screen having an intraoral operatory light suspended over a patient chair such that the display screen and operatory light are visible from the chair to provide unobstructed viewing of the display screen by the patient and to provide light into the patient's mouth without interfering with access to the patient's mouth by the dental staff; and
a controller configured to enable input commands by a patient through the controller to a computer associated with the display screen to provide patient access to a computer network.

17. The patient communication system of claim 16, further comprising directional speakers located in the patient chair, the directional speakers configured to provide sound in limited directions.

18. The patient communication system of claim 16, further comprising a video camera mounted in association with the display screen and for providing real time imaging.

19. The patient communication system of claim 16, further comprising at least one additional controller remote from the armrest of the chair to enable a service provider to control the display screen.

* * * * *